(12) United States Patent
Lichtenberg et al.

(10) Patent No.: US 11,634,260 B2
(45) Date of Patent: Apr. 25, 2023

(54) TRANSPORT DEVICE WITH AN INNER CONTAINER

(71) Applicant: InSphero AG, Schlieren (CH)

(72) Inventors: Jan Lichtenberg, Unterengstringen (CH); Olivier Frey, Oberwil (CH); Wolfgang Moritz, Bellikon (CH); David Fluri, Riehen (CH)

(73) Assignee: INSPHERO AG, Schlieren (CH)

( * ) Notice: Subject to any disclaimer, the term of this patent is extended or adjusted under 35 U.S.C. 154(b) by 0 days.

(21) Appl. No.: 17/273,961

(22) PCT Filed: Sep. 5, 2019

(86) PCT No.: PCT/EP2019/073757
§ 371 (c)(1),
(2) Date: Mar. 5, 2021

(87) PCT Pub. No.: WO2020/049123
PCT Pub. Date: Mar. 12, 2020

(65) Prior Publication Data
US 2021/0245945 A1     Aug. 12, 2021

(30) Foreign Application Priority Data
Sep. 6, 2018 (EP) ........................... 8192892

(51) Int. Cl.
*B65D 77/04* (2006.01)
*B01L 9/00* (2006.01)
*C12M 1/00* (2006.01)

(52) U.S. Cl.
CPC .............. *B65D 77/04* (2013.01); *B01L 9/523* (2013.01); *B01L 9/527* (2013.01); *C12M 23/52* (2013.01); *B01L 2200/185* (2013.01)

(58) Field of Classification Search
CPC ......... B65D 77/04; B01L 9/523; B01L 9/527; B01L 9/52; B01L 2200/185;
(Continued)

(56) References Cited

U.S. PATENT DOCUMENTS

| 4,919,300 A | 4/1990 | Kristy |
| 6,490,880 B1 * | 12/2002 | Walsh ..................... A01N 1/02 |
| | | 62/371 |

(Continued)

FOREIGN PATENT DOCUMENTS

| CN | 1500707 A | 6/2004 |
| CN | 102036555 A | 4/2011 |

(Continued)

OTHER PUBLICATIONS

PCT, PCT/EP2019/073757 (WO 2020/049123), Sep. 5, 2019 (Mar. 12, 2020), InSphero AG.

*Primary Examiner* — Michael L Hobbs
(74) *Attorney, Agent, or Firm* — Ballard Spahr LLP (57) ABSTRACT

Disclosed herein is a transport device comprising a first section of an outer container comprising a shell on the inside having the shape of a spherical cap with an inner diameter and an opening, wherein the opening of the spherical cap faces upwards, and an inner container having an upper section, a lower section and an inner hollow volume defined thereby, wherein at least the lower section has a spherical shape on the outside, the outer diameter of which is smaller than the inner diameter of the spherical cap of the outer container. The inner container is suitable to be arranged in the spherical cap of the outer container in a freely pivotable fashion, and is capable of accommodating a payload.

15 Claims, 10 Drawing Sheets (58) Field of Classification Search
CPC ....... B01L 2200/147; B01L 2300/0663; B01L 2300/0829; B01L 2300/12; B01L 2300/1883; B01L 2300/1894; C12M 23/52; C12M 37/00; A01N 1/0273
See application file for complete search history.

(56) References Cited

U.S. PATENT DOCUMENTS

| | | | | |
|---|---|---|---|---|
| 6,673,594 | B1* | 1/2004 | Owen | A01N 1/0247 |
| | | | | 435/284.1 |
| 6,899,850 | B2* | 5/2005 | Haywood | B01L 3/502 |
| | | | | 422/561 |
| 2006/0121437 | A1* | 6/2006 | Poo | A01N 1/0263 |
| | | | | 435/1.1 |
| 2011/0281352 | A1* | 11/2011 | Raeder | A01N 1/02 |
| | | | | 435/374 |

FOREIGN PATENT DOCUMENTS

| | | | |
|---|---|---|---|
| CN | 205872862 U | 1/2017 | |
| CN | 205879652 U | 1/2017 | |
| FR | 8585827 A2 | 3/1925 | |
| GB | 908835 A | 10/1962 | |
| GB | 2494651 * | 3/2013 | ............ B65D 77/04 |
| GB | 2494651 A2 | 3/2013 | |
| JP | H0831924 A | 7/2004 | |
| NL | 1033089 C2 | 6/2008 | |
| WO | 2011147384 A2 | 12/2011 | |
| WO | WO-2011/147384 A2 | 12/2011 | |

* cited by examiner

Figure 7A:
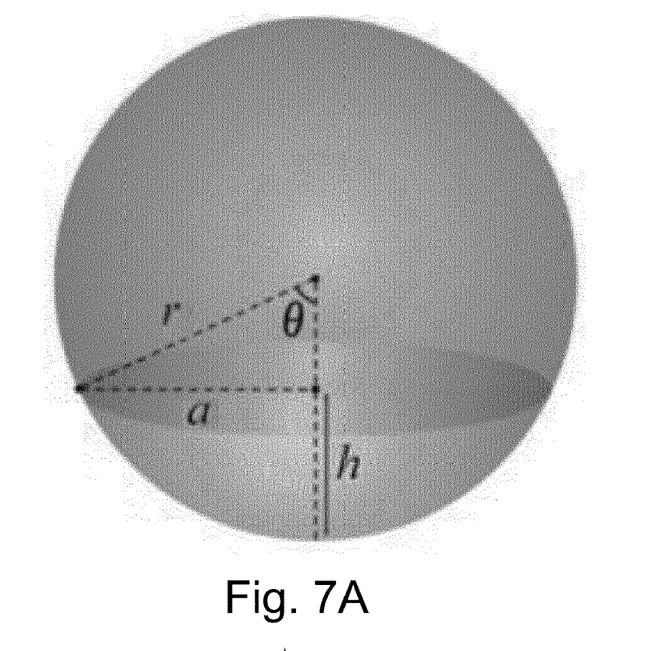
Figure 7B:
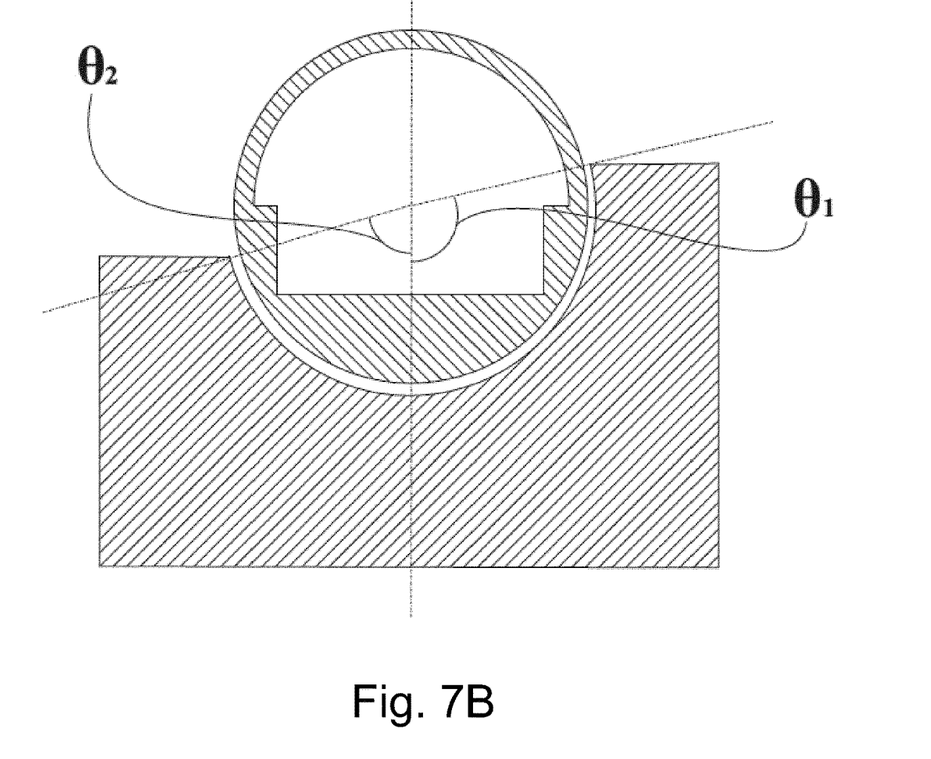

Fig. 7B

TRANSPORT DEVICE WITH AN INNER CONTAINER

CROSS-REFERENCE TO RELATED PATENT APPLICATIONS

This application is a national phase application under 35 U.S.C. § 371 of International Application No. PCT/EP2019/073757, filed Sep. 5, 2019. The content of this earlier filed application is hereby incorporated by reference in its entirety.

FIELD OF THE INVENTION

The present application relates to a transport device with an inner container.

BACKGROUND

Very often delicate goods are shipped to customers by usual mail services. In the course of such shipping, the respective transport boxes are often tilted, which may affect the goods transported therein.

One example for such delicate goods are biological specimen, like e.g. tissue samples, or microtissues. These are often stored and shipped in microwell plates often sealed by a sealing film or cover. When the surrounding transport box is tilted during transport, the microwell plate is tilted as well, and the culture liquid and the biological specimen fall out of the bottom of the microwell and move towards the top of the plate. Under unfavorable conditions the biological specimen can come into contact with the sealing film or cover, can attach to it or can be trapped between the sealing film and the upper wall of the microwell. Trapping or the contact with the sealing film can have adverse effects on the microtissue.

When the surrounding transport box is turned back into a horizontal position, the biological specimen may not return into the central groove, while the culture liquid does. As a consequence, the biological specimen may experience harm, or may even die.

If the biological specimen is attached to the bottom, tilting may move the liquid to the upper part of the well separating it from the biological specimen. This can lead to drying out of the biological specimen, nutrient depletion, and finally death.

In another example the goods are microplates, microfluidic chips or cell culturing dishes filled with a defined amount of liquid with or without biological specimen. If such good are only covered by a lid or the sealing is not complete liquid tight (in some cases by purpose to ensure gas exchange), tilting will lead to spillage or the liquid running out of its well or channels.

For other delicate goods to be shipped similar considerations apply when the transport box is tilted.

It is hence one object of the present invention to provide a transport device that protects the transported goods from negative effects when the device is tilted during transport.

It is one further object of the present invention to provide a transport device that allows safe shipment of delicate goods, including biological specimen and not fully sealed devices, in which tilting my lead to liquid spillage or drainage.

These and further objects are met with methods and means according to the independent claims of the present invention. The dependent claims are related to specific embodiments.

DETAILED DESCRIPTION OF THE FIGURES

It is important to understand that most figures show a two-dimensional cross section of a transport device according to the invention, which is a three-dimensional object. Hence, considerations and discussions made with regard to the figures apply to a three-dimensional object.

FIG. 1 is provided to demonstrate a fundamental problem that occurs when microwell plates are tilted.

Figure 1A:
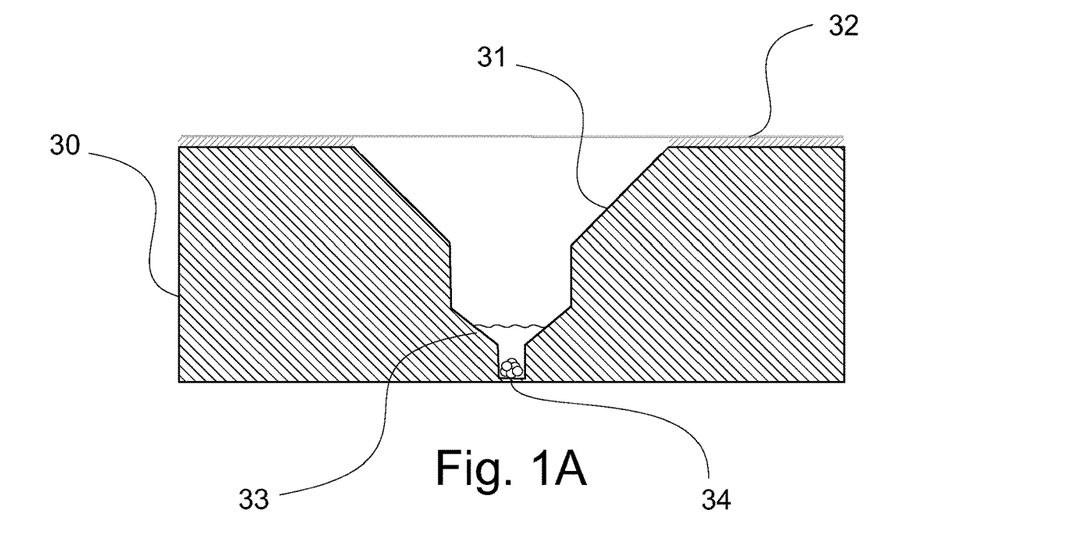

FIG. 1A shows a close-up of a microwell plate 30 with one well 31 shown. The well is sealed by a sealing film 32 and has a central groove where a biological specimen 34, e.g., a microtissue, is disposed, and covered by culture liquid 35.

Figures 1B, 1C:
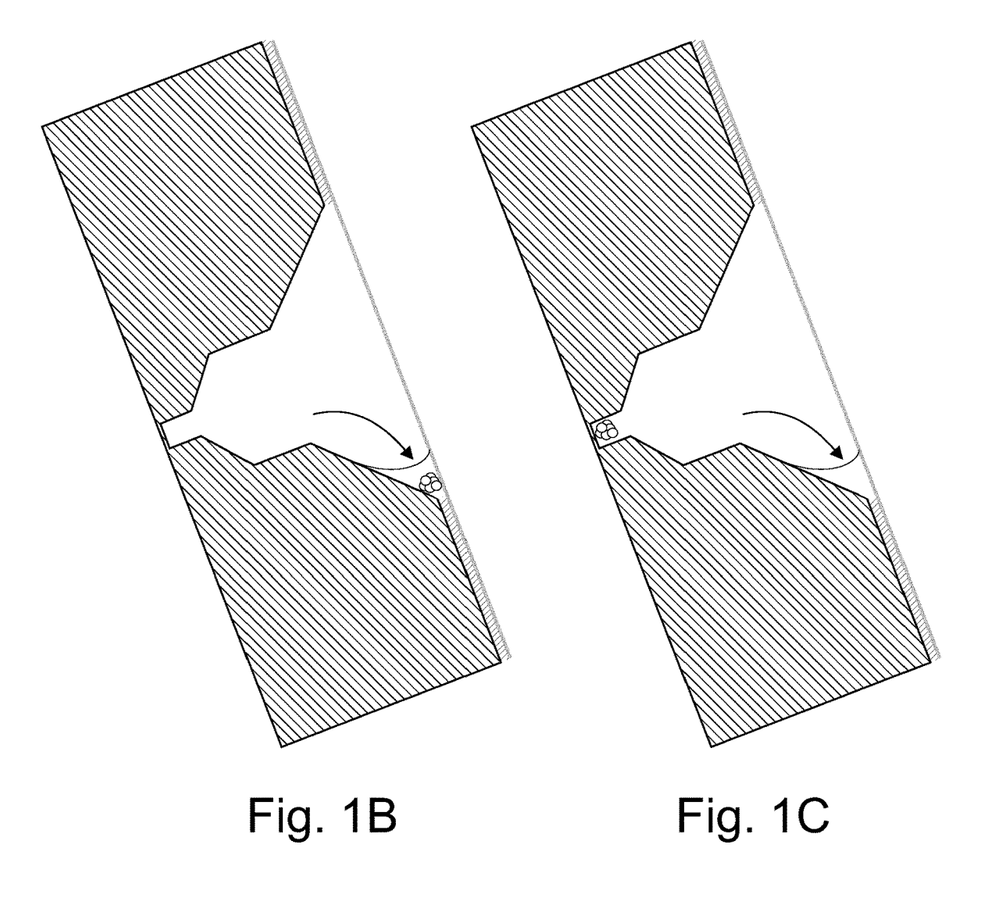

FIG. 1B shows what happens when the microwell plate is tilted. The culture liquid and the biological specimen fall out of the central groove (see arrow), and under unfavorable conditions the biological specimen can be trapped between the sealing film and the upper wall of the well. Even though such film can be made from a biocompatible material, the microtissue might either adhere thereto or be squeezed in the angle formed by the film and the well's wall. When the microwell plate is turned back into a horizontal position, the biological specimen may not return into the central groove, while the culture liquid does. As a consequence, the biological specimen may experience harm, or may even die. It has to be noted that such problem mostly applies to biological specimens that are not attached to the bottom.

FIG. 1C shows what can happen with biological specimens that are attached or adhere to the culturing in case the microwell plate is tilted. In such case, the culturing liquid moves to the top of the well, leaving the biological specimen dry at the bottom of the well.

Another problem might occur when a sealing film, or more generally a lid or cover, is chosen which is not totally liquid tight, but just protects from spillage or ensures oxygen supply (having small holes for example). Prolonged tilting would lead to complete drainage of the well. As a consequence, the biological specimen may experience harm, or may even die.

FIG. 2 shows a transport device 10 according to the invention, comprising a first section 11a of an outer container. The first section comprises a shell on the inside having the shape of a spherical cap 12a, with an inner diameter and an opening. The opening 13 of the spherical cap faces upwards. The device further comprises an inner container 14 having an upper section 15b a lower section 15a and an inner hollow volume 16 defined thereby. The lower section has a spherical shape on the outside, the outer diameter of which is smaller than the inner diameter of the spherical cap 13. The inner container is suitable to be arranged in the spherical cap of the outer container in a freely pivotable fashion. The inner container is capable of accommodating a payload 17, namely a microtiter plate that accommodates microtissues. The inner container is designed in such way, or a counterweight is arranged in the inner container in such way, that the center of gravity 22 of the inner container, when containing a payload, is arranged eccentrically below the inner container's rotational center 23. Further, an interstice 18 is defined between the inner diameter of the spherical cap of the first section of the outer container and the outer diameter of the spherical shape of the inner container. A volume of liquid 19 is disposed in said interstice, which reaches maximally to a height of 2.3% of the inner container. It can clearly bee seen that the inner container floats on the volume of liquid. In such way, sufficient degrees of freedom are provided for the inner container to float. Likewise, friction between the surfaces is reduced to a minimum.

Figure 2A:
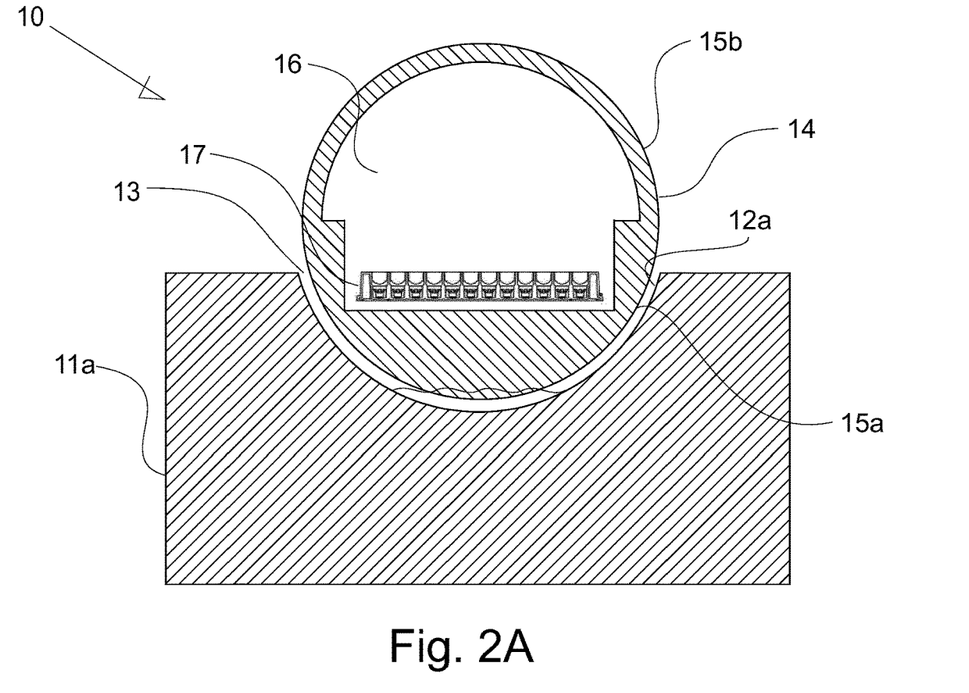
Figure 2B:
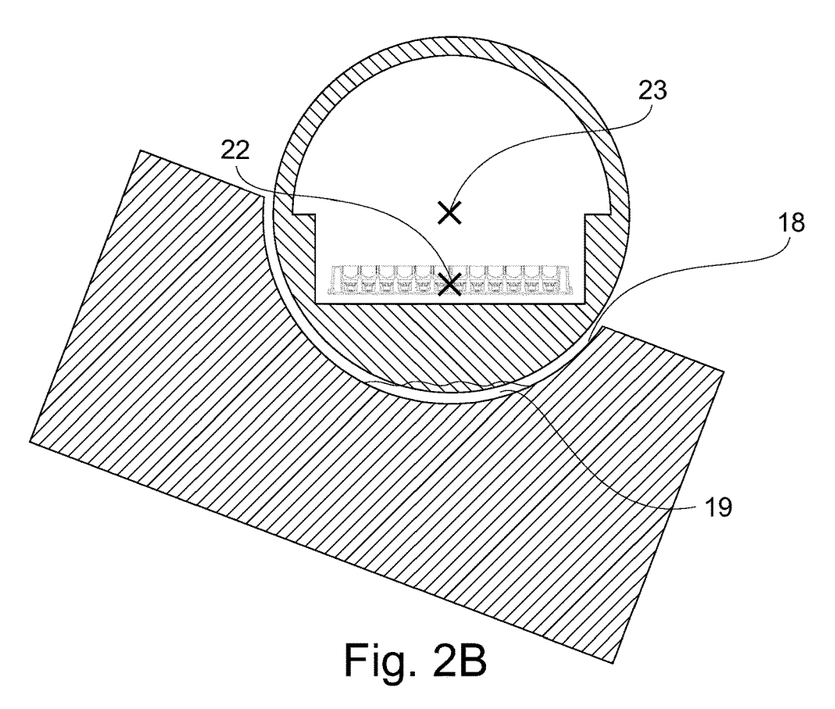

In FIG. 2A, the device is shown in a normal position, while in FIG. 2B the device is tilted by an angle of about 20°. It is clearly visible that despite the fact that the outer container is tilted, the inner container adopts an upright position.

Figure 2C:
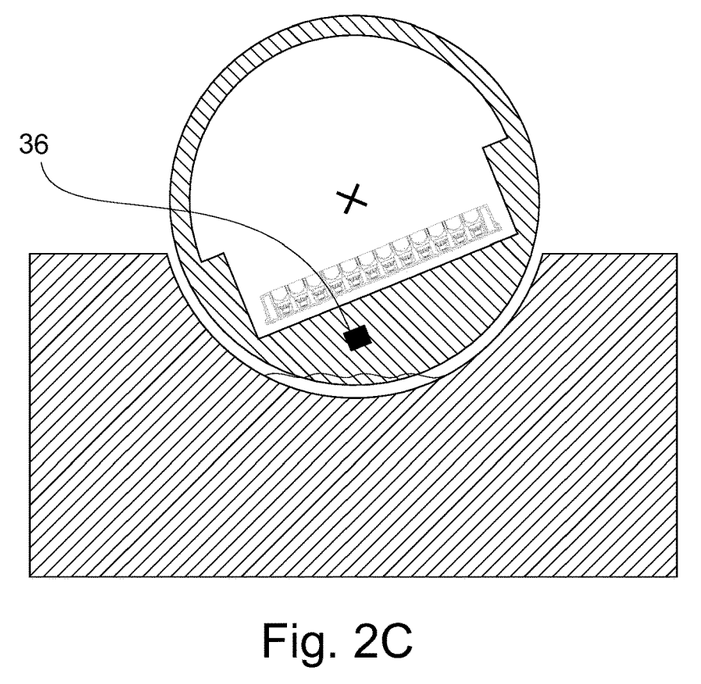
Figure 2D:
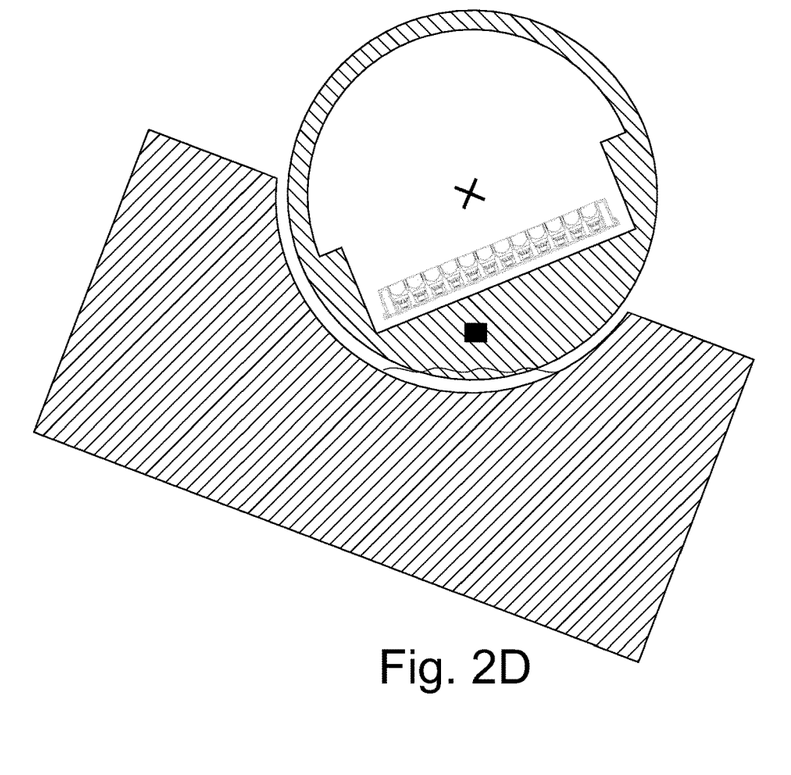

FIGS. 2C, D, E and F show further embodiments. FIGS. 2C and D show an embodiment in which the center of gravity of the inner container has a lateral offset, as, e.g., caused by a specific counterweight 36, arranged below the inner container's center, but offset of the vertical axis. In this embodiment, the inner container permanently adopts a defined tilted angle when in resting position, independent of the orientation of the outer container (FIG. 2C: Horizontal, FIG. 2D: tilted). In such way, a gravity-driven flow in a microwell plate or a microfluidic chip comprised in the inner container can be for example be established.

Figure 2E:
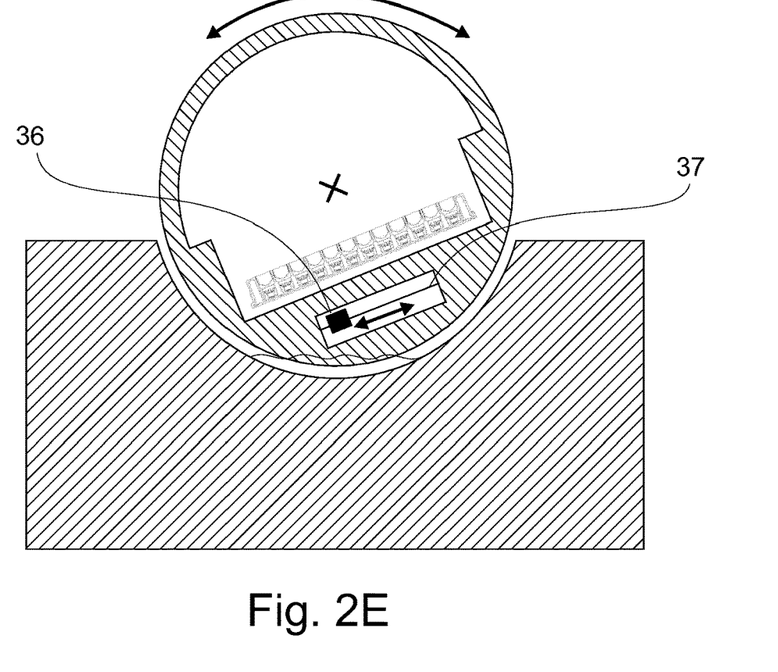

FIG. 2E shows an embodiment in which the center of gravity of the inner container can be changed, e.g., caused by a specific counterweight 36 that is continuously agitated in a lateral fashion, by a suitable linear actuator 37. In this embodiment, the inner container is subjected to a rocking movement, independent of the orientation of the outer container. In such way, liquids and/or biological specimen comprised in the inner container can be agitated.

Figure 2F:
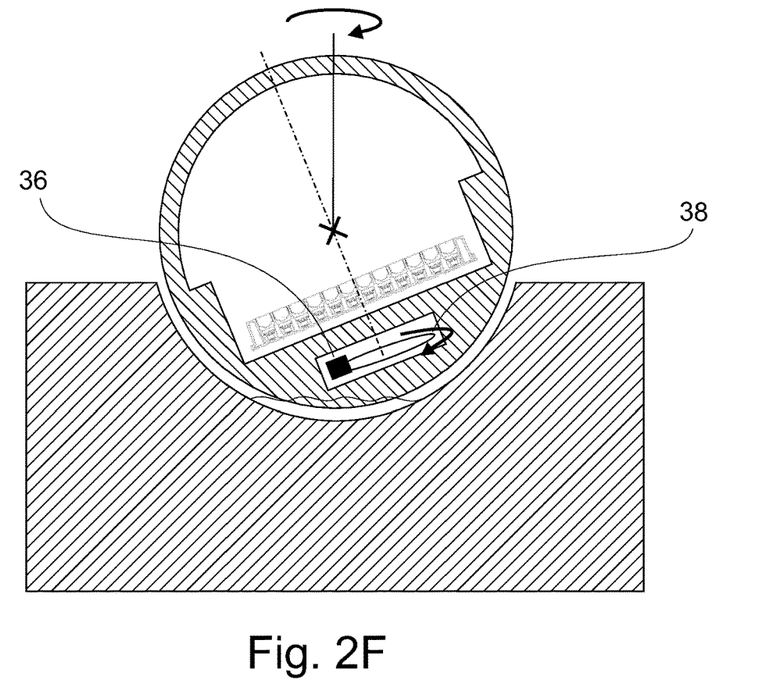

FIG. 2F shows an embodiment in which the center of gravity of the inner container can be changed, e.g., caused by a specific counterweight 36 that is continuously agitated in a circular fashion, by a suitable circular actuator 38. In this embodiment, the inner container is subjected to a circular rocking movement, independent of the orientation of the outer container. In such way, liquids and/or biological specimen comprised in the inner container can be agitated.

Figure 3A:
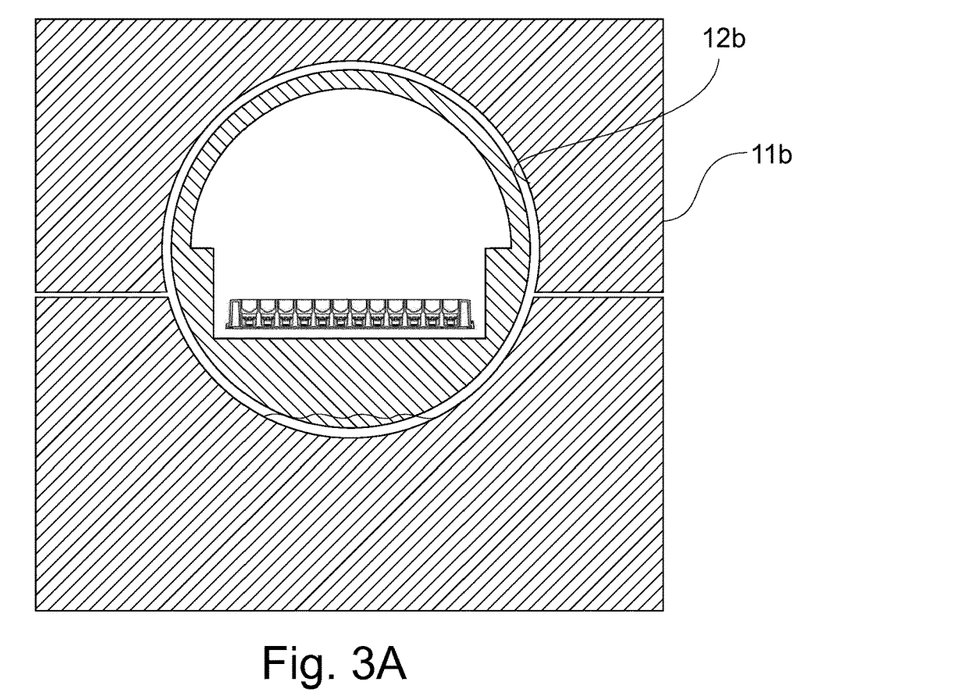

FIG. 3A shows a similar transport device according to the invention, wherein further the outer container comprises a second section 11b comprising a shell on the inside having the shape of a spherical cap 12b, with an inner diameter and an opening, wherein the opening of the spherical cap faces downwards.

Figure 3B:
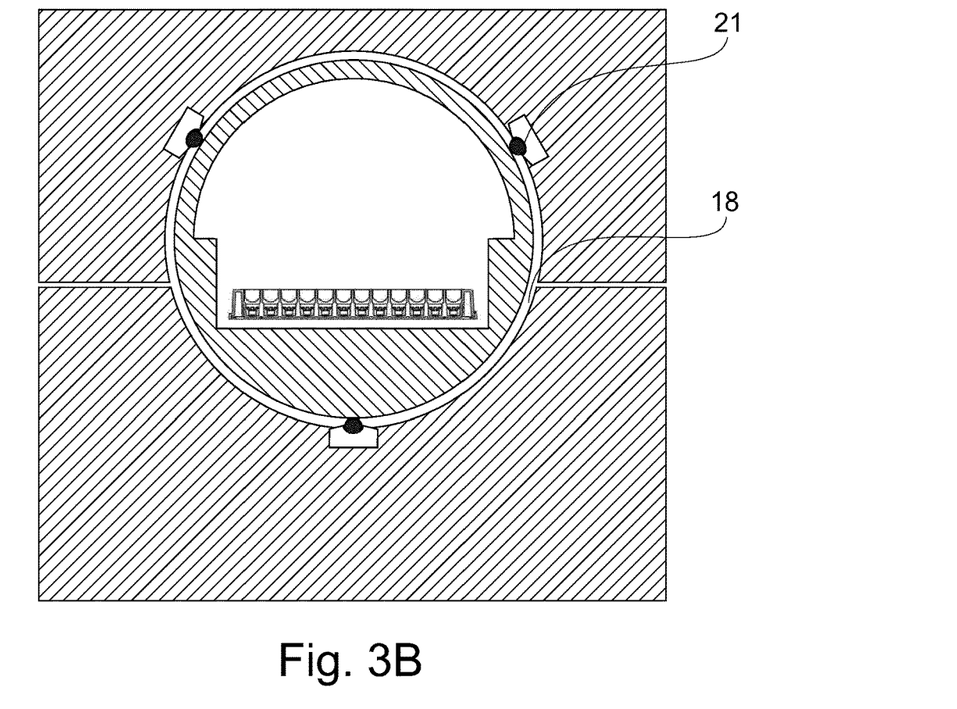

FIG. 3B shows a similar transport device according to the invention, wherein three ball bearings 21 are disposed in the interstice 18. The width of the interstice 18 depends on the length ball bearings extend into the interstice (see arrow).

Figure 4A:
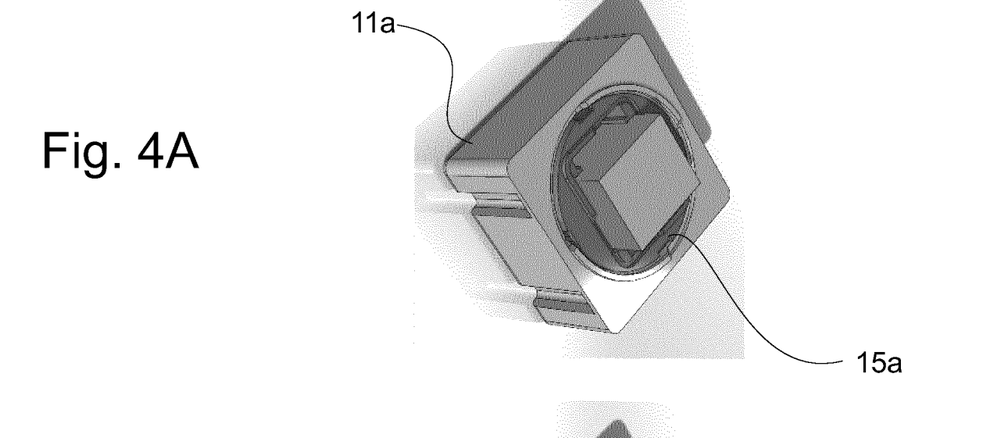
Figure 4B:
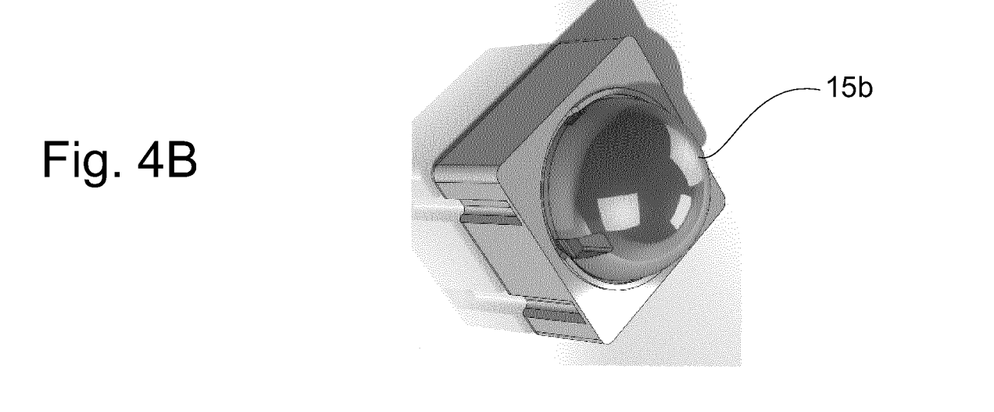
Figure 4C:
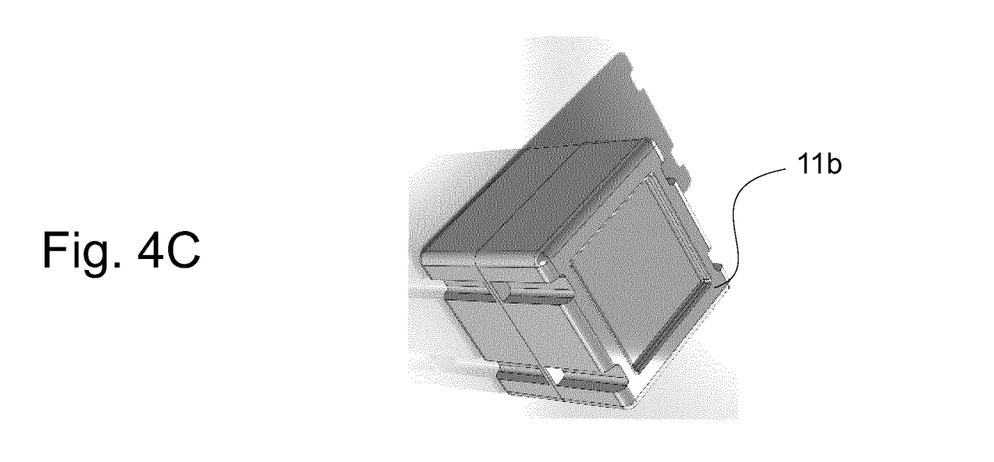
Figure 5:
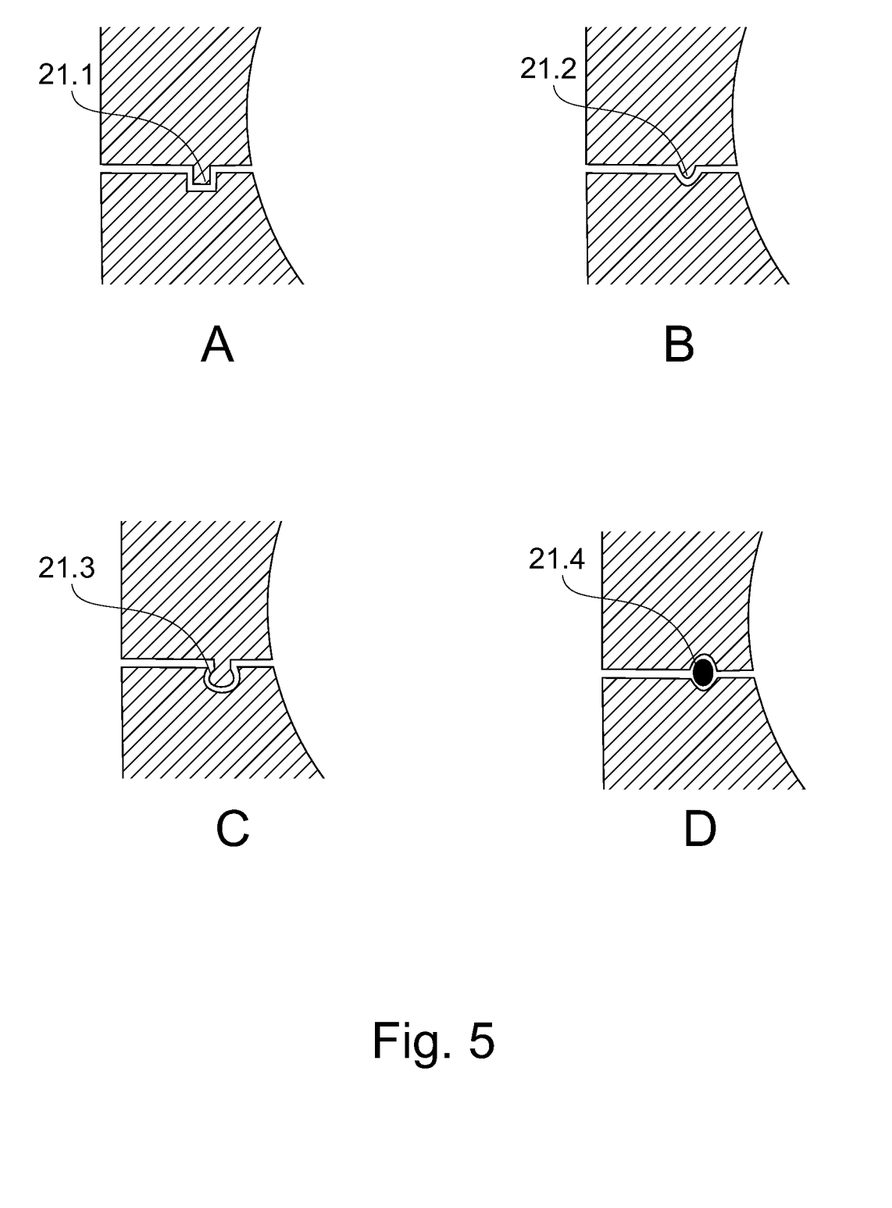

FIGS. 4A-C show three dimensional renderings of a transport device according to the invention. The two sections 11a, 11b of the outer container are made from extruded polystyrene foam, as are the two sections 15a, 15b of the inner container. FIG. 4A also shows a box in the center, which is the actual transported good in the present example. The box can comprise, e.g., biological specimen.

FIGS. 5A-D show different possibilities to connect the two sections 11a, 11b of the outer container with a tongue-and-groove joint 21.1, 21.2, 21.3, and with an O-Ring 21.4.

The tongue can be bigger than the groove, so that it needs to be pressed in to ensure tightness. The grove can also be left away so that the tongue has to be deformed for tightness.

FIG. 6 shows acceleration data measured from test shipments of a prototype using the floating sphere concept.

FIG. 7A shows the dimensions that are necessary to define the spherical cap of the transport device according to the present invention, as shown in grey shade.

The term "spherical cap", as used herein, is used interchangeably with the terms "spherical dome", or "spherical segment", and relate to a portion of a sphere cut off by a plane. If the plane passes through the center of the sphere, so that the height of the cap (h) is equal to the radius (r) of the sphere, the spherical cap is called a hemisphere. In such case, the angle θ would assume 90°. In most cases, θ will be in the range of 45-89°, so that the inner container can easily be deposited in, or removed from, the shell on the inside of the first section of the outer container.

FIG. 7B shows two alternatives, namely one (left side) where $\theta_2$ is smaller than 90° (hence the inner container can easily be deposited in, or removed from, the shell on the inside of the first section of the outer container), and one (right side) where $\theta_2$ is greater than 90° (hence the inner container rests more securely in the shell on the inside of the first section of the outer container, but can less easily be deposited therein, or removed therefrom).

DETAILED DESCRIPTION OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a", "an", and "the" include singular and/or plural referents unless the context clearly dictates otherwise. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the prior art documents referred to herein is incorporated by reference. This refers, particularly, for prior art documents that disclose standard or routine methods. In that case, the incorporation by reference has mainly the purpose to provide sufficient enabling disclosure, and avoid lengthy repetitions.

According to a first aspect of the invention, a transport device is provided, comprising a) a first section of an outer container comprising a shell on the inside having the shape of a spherical cap, with an inner diameter and an opening, wherein the opening of the spherical cap faces upwards, b) an inner container having an upper section a lower section and an inner hollow volume defined thereby, wherein at least the lower section has a spherical shape on the outside, the outer diameter of which is smaller than the inner diameter of the spherical cap of the outer container, c) the inner container being suitable to be arranged in the spherical cap of the outer container in a freely pivotable fashion.

d) the inner container being capable of accommodating a payload.

The shell on the inside of the first section of the outer container, with its spherical cap-like shape, has a three dimensional concave form (i.e., is curved inward). The lower section of the inner container, with its spherical shape on the outside, has a three dimensional convex form (i.e., is curved outward).

The term "spherical cap", as used herein, is used interchangeably with the terms "spherical dome", or "spherical segment", and relate to a portion of a sphere cut off by a plane. If the plane passes through the center of the sphere, so that the height of the cap (h) is equal to the radius (r) of the sphere, the spherical cap is called a hemisphere. In such case, the angle θ would assume 90°. See FIG. 7A for an explanation.

It has to be mentioned that high tolerances can be accepted as regards the spherical properties. The shells do not need to be "super strictly" spherical. The general shape needs to be spherical, but there can be irregularities, like notches or recesses, which allow holding the sphere or that may have been introduced by the fabrication process. The size of them should be as small as the general function of free rotation and upright orientation of the inner container is always given.

The shell on the inside of the first section of the outer container thus serves as a bed for the inner container with its spherical shape. In most cases, θ will be in the range of 45-89°, so that the inner container can easily be deposited in, or removed from, the shell on the inside of the first section of the outer container.

In one aspect, the shell on the inside of the first section of the outer container acts like a socket in a ball and socket joint, while the inner container, with its spherical shape on the outside, acts like a ball which rests in said socket.

According to one embodiment of the invention, the inner container is designed in such way, or a counterweight is arranged in the inner container in such way, that the center of gravity (22) of the inner container, when containing a payload, is arranged eccentrically below the inner container's rotational center (23).

The center of gravity of the inner container is arranged eccentrically, and below the inner container's rotational center. In such way, because the inner container is freely movable in the shell on the inside of the outer container, it is, by gravity, capable of maintaining, or reestablishing, an upright position even when the outer container is tilted.

See, in this regard FIGS. 2 C-E, which show variables of this embodiment, in which (a) the center of gravity of the inner container has a lateral offset, so that the inner container adopts a defined tilted angle when in resting position, independent of the orientation of the outer container), or (b) the center of gravity of the inner container is periodically moved in a lateral or circular fashion using a suitable actuator, so that the payload is continuously agitated.

According to a further embodiment of the invention, an interstice is defined between the inner diameter of the spherical cap of the first section of the outer container and the outer diameter of the spherical shape of the inner container.

According to a further embodiment of the invention, a volume of liquid is disposed in said interstice. Preferably, said liquid is hydrophilic, more preferably said liquid is water.

The term "hydrophilic", as used herein, relates to molecules or other molecular entities that are attracted to water molecules and tend to be dissolved by water. They are typically charge-polarized and capable of hydrogen bonding. Hydrophilic liquids comprise such polar molecules and are thus also capable of hydrogen bonding. This especially applies to water, but also to (low) alcohols. Water ($H_2O$) is a polar inorganic compound that is at room temperature a tasteless and odorless liquid. Water molecules form hydrogen bonds with each other and are strongly polar. Alcohols comprise hydroxyl groups that are polar and therefore hydrophilic but also comprise a carbon chain portion that is non-polar, i.e. hydrophobic. The alcohol molecule increasingly becomes overall more hydrophobic as the carbon chain becomes longer. Examples of hydrophilic liquids include, but are not limited to, water, alcohols, ammonia, some amides such as urea and some carboxylic acids such as acetic acid.

According to a further embodiment of the invention, the surface of the inner container and/or the outer container is hydrophobic.

The term "hydrophobic", as used herein, relates to molecules or other molecular entities that are repelled from water molecules. They are nonpolar and, thus tend to be not dissolved in water but prefer other neutral molecules and nonpolar solvents. Hydrophobic surfaces have the ability to repel water. Generally, the hydrophobicity of a surface can be measured by the contact angle between the droplets of water with the surface itself. The water droplets on hydrophobic surface will flow very easily and retain its spherical shape with contact angle more than 90 degrees [8], while superhydrophobic materials possess large contact angles above 150 degrees and difficult to wet. Examples of hydrophobic molecules include the alkanes, oils, fats, and greasy substances in general.

According to a further embodiment of the invention, the inner container has a lower specific weight than said liquid.

The term "specific weight", as used herein, is defined as weight per unit volume of a material. The symbol of specific weight is γ (the Greek letter Gamma). The SI unit for specific weight is [$N/m^3$]. Specific weight can be expressed as $$\gamma = \rho a_g$$

where
γ=specific weight ($N/m^3$)
ρ=density [$kg/m^3$]
$a_g$=acceleration of gravity (9.81 [$m/s^2$], under normal conditions)

The following table shows the specific weights of some common materials.

| Product | Specific weight [$kN/m^3$] |
| --- | --- |
| Air | 0.011772 |
| Aluminum | 27 |
| Copper | 89 |
| Ethyl Alcohol | 7.74 |
| Seawater | 10.03 |
| Stainless Steel | 78-80 |
| Water | 9.81 |
| extruded polystyrene foam | 0.4905 |
| expanded polystyrene (EPS) | 0.0108-0.0314 |
| expanded polypropylene (EPP) | 0.1196-0.1177 |
| wood | 4.6107-10.3986 |
| Thermoplasts | 7.848-21.582 |
| Teflon | 21.582 |

According to a further embodiment of the invention, the lower specific weight of the inner container creates buoyancy of the inner container.

Archimedes' principle states that the upward buoyant force that is exerted on a body immersed in a fluid, whether fully or partially submerged, is equal to the weight of the fluid that the body displaces and acts in the upward direction at the center of mass of the displaced fluid. Thus, if the specific weight of an object is lower than the specific weight of water, the object will float on the water surface.

In this embodiment, the inner container floats on said liquid, hence avoiding any friction between the inner container and the inner surface of the shell on the inside of the first section of the outer container. This enables the inner container to always maintain, or reestablish, an upright position even when the outer container is tilted.

According to a further embodiment of the invention, the outer container is maximally half filled with said liquid.

In this embodiment, the filling level of said liquid ensures that the inner container floats within said liquid. Thus, said liquid serves to exert buoyancy and does not serve as a lubricant. Since there is no direct contact between the surface of the inner container and the surface of the shell on the inside of the second section of the outer container, there is also no friction in said areas. This enables the inner container to always maintain, or reestablish, an upright position even when the outer container is tilted.

The term "half filled with liquid" means that the liquid, once the inner container is disposed in the outer container, reaches only to the equator of the inner container.

Preferably, the outer container is maximally filled by 25%, preferably maximally 15%, more preferably maximally 10%, more preferably maximally 5%, more preferably maximally 2% filled with water. In all the cases, the liquid, once the inner container is disposed in the outer container, reaches maximally up to a height of 25, 15, 10, 5, or 2% of the inner container.

According to a further embodiment of the invention, a lubricant is disposed in said interstice. Said lubricant as well reduces the friction between the inner container and the inner surface of the shell on the inside of the first section of the outer container. This enables the inner container to always maintain, or reestablish, an upright position even when the outer container is tilted.

According to a further embodiment of the invention, at least two balls or ball bearings are disposed in said interstice. The balls as well reduce the friction between the inner container and the inner surface of the shell on the inside of the first section of the outer container. This enables the inner container to always maintain, or reestablish, an upright position even when the outer container is tilted.

According to a further embodiment of the invention, at least
a) the inner surface of the shell on the inside of the first section of the outer container, and
b) the outer surface of the lower section of the inner container comprise materials that, when acting with one another, establish a low friction coefficient.

The term "low friction coefficient" relates to static friction ($\mu_s$). Preferably, the coatings that are used, when acting with one another, establish a friction coefficient of <0.2$\mu_s$ or less. The said condition applies, for example, to the following material pairs:

| Materials and Material Combinations | | Static Frictional Coefficient ($\mu_s$) |
|---|---|---|
| Bronze | Steel | |
| Bronze | Cast Iron | 0.22 |
| Bronze-sintered | Steel | |
| Carbon (hard) | Carbon | 0.16 |
| Carbon | Steel | 0.14 |
| Copper-Lead alloy | Steel | 0.22 |

-continued

| Materials and Material Combinations | | Static Frictional Coefficient ($\mu_s$) |
|---|---|---|
| Diamond | Diamond | 0.1 |
| Diamond | Metal | 0.1-0.15 |
| Graphite | Steel | 0.1 |
| Graphite | Graphite | 0.1 |
| Nylon | Nylon | 0.15-0.25 |
| Polythene | Steel | 0.2 |
| Sapphire | Sapphire | 0.2 |
| Polytetrafluoro ethylene (PTFE) | PTFE | 0.04 |
| PTFE | Steel | 0.05 |
| Tungsten Carbide | Tungsten Carbide | 0.2-0.25 |
| Wax | Wax | 0.25 |

In such way, the friction between the inner container and the inner surface of the shell on the inside of the first section of the outer container is reduced. This enables the inner container to always maintain, or reestablish, an upright position even when the outer container is tilted.

The width of the interstice can depend on the material that is disposed between the surfaces of the shell on the inside of the first section of the outer container and the lower section of the inner container.

According to one embodiment, the width of the interstice in which the volume of liquid is applied is in the range of ≥2 mm and ≥15 mm, so as to allow floating of the inner container. In such way, sufficient degrees of freedom are provided for the inner container to float. Likewise, friction between the surfaces is reduced to a minimum. Further, such relatively wide interstices make the production of the inner- and outer container more easy, because higher tolerances are admissible.

In this embodiment, due to the large width of the interstice, there is no direct contact between the surface of the inner container and the surface of the shell on the inside of the first and the second section of the outer container, therefore there is no friction between the inner and the outer container. This enables the inner container to always maintain, or reestablish, an upright position even when the outer container is tilted.

In one embodiment, the width of the interstice in which a lubricant is applied is almost infinitesimally small, with the usual tolerances, so that the two surfaces are only separated from one another by a thin film of lubricant. Generally, the use of a lubricant requires that the width of the interstice is smaller than if a volume of liquid would be applied. This again makes the manufacturing process more demanding. In one embodiment, the interstice is not wider than 2 mm.

In one embodiment, which comprises balls or ball bearings, the width of the interstice depends on the length the balls or ball bearings extend into the interstice (see e.g. FIG. 3B), plus tolerances if applicable.

In one embodiment, which comprises surfaces that establish a low friction coefficient, the width of the interstice can be infinitesimally small (with the usual tolerance), so that the two surfaces are in direct contact to one another. Generally, such embodiment makes the manufacturing process highly demanding.

In one embodiment, the width of the interstice is not wider than 2 mm, preferably not wider than 1.5 mm, most preferably not wider than 1 mm.

According to a further embodiment of the invention, the inner container and/or the outer container comprises a material that is a thermal insulator.

The term "thermal insulator", as used herein, refers to and object or material that provides the reduction of heat transfer, i.e. the transfer of thermal energy between objects of differing temperature, between objects in thermal contact or in range of radiative influence. Thermal insulation can be achieved with specially engineered methods or processes, as well as with suitable object shapes and materials.

The insulating capability of a material is measured as the inverse of thermal conductivity (k). Low thermal conductivity is equivalent to high insulating capability (Resistance value). Thermal conductivity k is measured in watts-per-meter per kelvin ($W \cdot m^{-1} \cdot K^{-1}$ or W/m/K). Thermal conductivity depends on the material and for fluids, its temperature and pressure. For comparison purposes, conductivity under standard conditions (20° C. at 1 atm) is commonly used. For some materials, thermal conductivity may also depend upon the direction of heat transfer.

The following table shows thermal conductivity for some materials at atmospheric pressure and around 293 K (20° C.).

| Material | Thermal conductivity [$W \cdot m^{-1} \cdot K^{-1}$] |
| --- | --- |
| Silica aerogel | 0.02 |
| Polyurethane foam | 0.03 |
| Expanded polystyrene | 0.033-0.046 |
| Fiberglass or foam-glass | 0.045 |
| Alcohols, oils | 0.100 |
| Snow (dry) | 0.050-0.250 |
| Acrylic glass (Plexiglas V045i) | 0.170-0.200 |
| Teflon | 0.250 |
| Water | 0.5918 |
| Marble | 2.070-2.940 |
| Manganese | 7.810 |
| Alumina | 30 |
| Aluminium | 237 |
| Copper(pure) | 401 |
| Diamond | 1.000-2200 |
| Boron arsenide | 1.300 |

According to a further embodiment of the invention, the outer container further comprises a second section comprising a shell on the inside having the shape of a spherical cap, with an inner diameter and an opening, wherein the opening of the spherical cap faces downwards. This section acts as a lid for the container, and provides insulation and protection.

Said spherical cap has essentially the same radius as the spherical cap comprised in the first section of the outer container. When the second section of the outer container is arranged on top of the first section, the two hemispherical caps form a sphere. In such embodiment, the inner container is fully protected when the outer container is not just tilted a couple of degrees but either 90° or 180° degrees, ultimately requiring that the inner section can rotate 360° and is always upright.

According to a further embodiment of the invention, device further comprises at least one selected from the group consisting of
a) a heating unit,
b) a cooling unit
c) a temperature sensor and/or recorder,
d) an acceleration sensor and/or recorder,
f) a geolocalization sensor and/or recorder,
g) an identifiable tag or label
h) mechanical actuator for moving the center of gravity with respect to the center of the sphere The heating unit and/or the cooling unit can comprise a thermal pack, comprising, e.g., ice or dry ice, or so-called fluid elements, as produced by delta T GmbH, Fernwald. The heating unit and/or the cooling unit can also comprise a thermoelectric element, e.g., a Peltier element.

The temperature sensor and/or recorder can be any suitable sensor and/or recorder (also called "logger") that is available in the art. It is preferably battery driven and covers a temperature range of between −50 and +50° C.

The acceleration sensor and/or recorder can be any suitable sensor and/or recorder (also called "logger") that is available in the art. Such acceleration sensors and/or recorders are for example built in most mobile telecommunication devices available in the art.

The geolocalization sensor and/or recorder can be any suitable sensor and/or recorder (also called "logger") that is available in the art. Such geolocalization sensors and/or recorders are for example built in most mobile telecommunication devices available in the art.

The identifiable tag or label can be any tag or label that provides a digital signature readable by a suitable device. Such tag or label can be a barcode or QR code that can be identified with a suitable optical reader, but can also be a tag or label that can be read out by radio-frequency identification (RFID) or near field communication (NFC).

The mechanical actuator can battery-driven and can be a mechanical rotor with an eccentric load or a linear motor moving a load back and forth in a continuous pre-programmed way or remotely controlled.

According to a further embodiment of the invention, the payload double acts as a counterweight. This facilitates the entire production process.

According to a further embodiment of the invention the payload is at least one selected from the group consisting of
one or more multiwell plates or microtiter plates, or a container comprising one or more such plates
a microfluidic system or microfluidic chips, and/or
cell culturing dishes and systems In general, the payload can be any payload requiring upright or stabilized shipment.

Preferably, the multiwell plates or microtiter plates or microfluidic chips or cell and tissue culturing dishes are plates that contain liquid/medium and comprise one or more cell, cell culture, microtissue, 3D tissue, spheroidal tissue, composite tissue, tissue sample, tissue slice, or the like.

According to a further embodiment of the invention, the outer container and/or the inner container comprise a material selected from the group consisting of
extruded polystyrene foam
expanded polystyrene (EPS)
expanded polypropylene (EPP)
metal
wood
thermoplasts
friction-minimizing material such as teflon

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these mea-

Example 1

A prototype of the transport device was developed and tested. The device was packed in a usual transport box which remained unopened the whole time.

Both sections of the outer and inner container were closed and sealed water-tight with silicone. Water was filled between the two shells enabling free rotation of the inner shell with respect to the outer shell. To record the orientation of the shells, one accelerometer was placed inside the box together with the shipped goods and one accelerometer was placed on the outside of the box. Upright orientation equals to a value of −1 g in z-direction and a value of 0 in x and y direction.

Figure 6A:
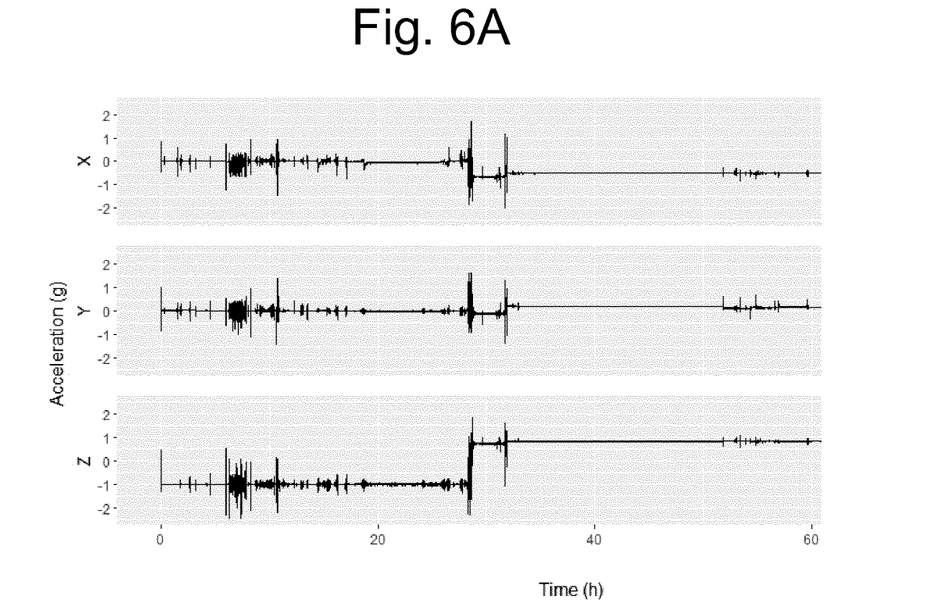
Figure 6B:
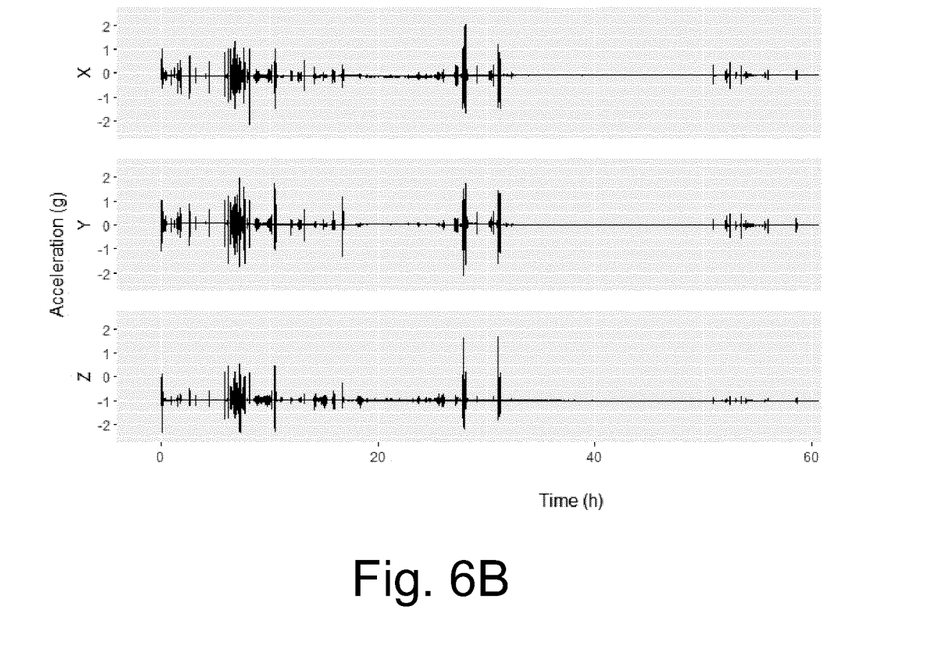

FIGS. 6A and 6B show data of a transatlantic flight cargo from Switzerland to US. The acceleration data of the box reveals that the box has been turned over and placed upside down after about 30 hours of travel. The inner floating sphere remained upside. The data in FIG. 6B shows a constant value of −1 for the acceleration in z-direction.

Figure 6C:
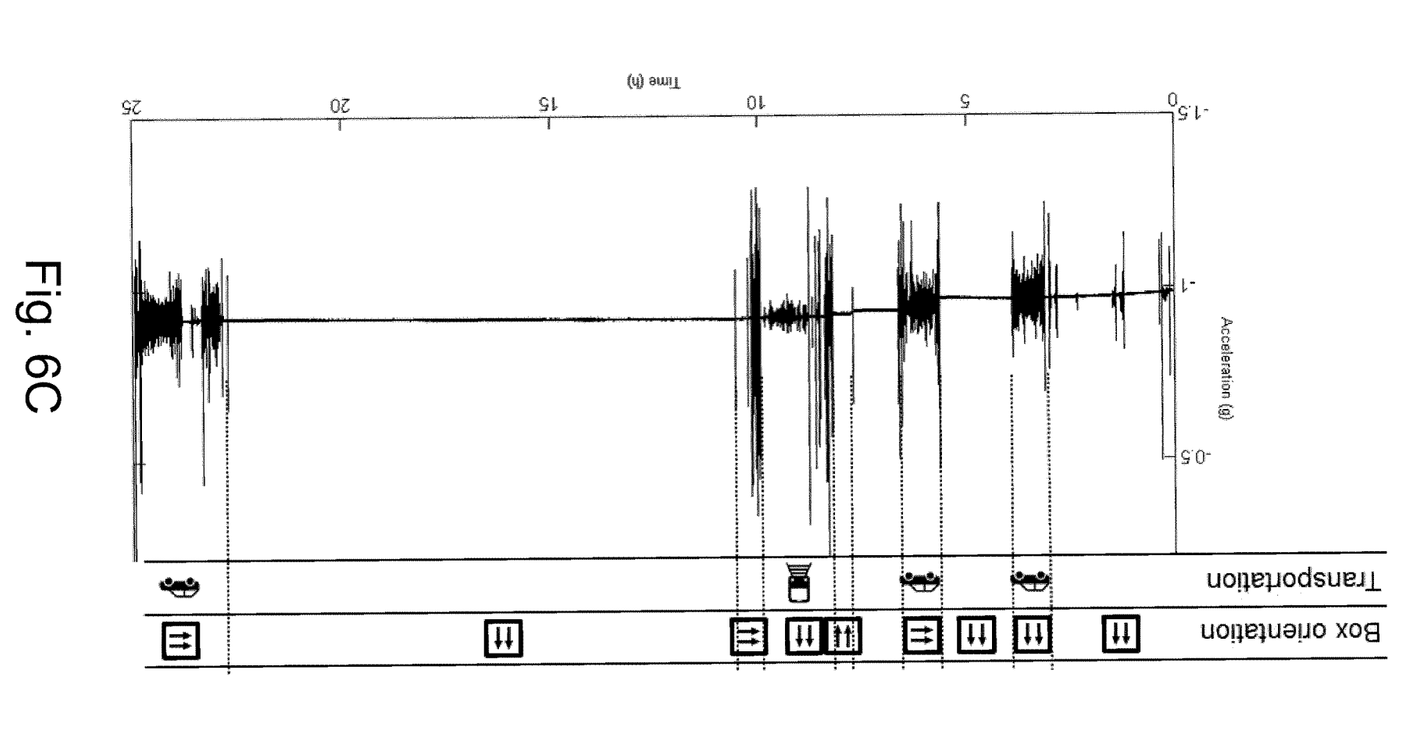

FIG. 6C presents data from a ground shipment simulation over 25 hours. Z-Acceleration data of the inside of the goods compartment is presented. Above the graph, the orientation of the outer box and transportation of the box is depicted. Tilting and flipping of the box was well compensated and the inner sphere remained in an upright position independent of transportation and orientation of the outside box.

REFERENCE NUMBERS 10 transport device
11 outer container
11a first section of outer container
11b second section of outer container
12a shell on the inside of outer container having the shape of a spherical cap
13 opening of shell 12a
14 inner container
15b upper section of inner container
15a lower section of inner container
16 inner hollow volume of inner container
17 payload
18 interstice
19 liquid disposed in interstice
20 ball bearing
21.1, 21.2, 21.3 tongue-and-groove joints
21.4 O-ring
22 center of gravity of inner container
23 rotational center of inner container
30 microwell plate
31 well
32 sealing film
33 central groove
34 biological specimen
35 culture liquid
36 counterweight
37 linear actuator
38 circular actuator

The invention claimed is:

1. A transport device (10), comprising
   a) a first section of an outer container comprising a shell on an inside of the outer container, the shell having the shape of a spherical cap with an inner diameter and an opening, wherein the opening of the spherical cap faces upwards,
   b) an inner container having an upper section a lower section and an inner hollow volume defined thereby, wherein at least the lower section has a spherical shape on the outside, the outer diameter of which is smaller than the inner diameter of the spherical cap of the outer container,
   c) the inner container being suitable to be arranged in the spherical cap of the outer container in a freely pivotable fashion,
   d) the inner container capable of accommodating a payload, and
   e) a liquid,
   wherein the inner container is designed in such way that by receiving a payload, the inner container and payload have a combined center of gravity that is arranged eccentrically and below the inner container's rotational center,
   wherein an interstice is defined between the inner diameter of the spherical cap of the first section of the outer container and the outer diameter of the spherical shape of the inner container,
   wherein the liquid is disposed in said interstice,
   wherein the inner container has a lower specific weight than said liquid, wherein the inner container floats on said liquid.

2. The transport device according claim 1, wherein said liquid is hydrophilic.

3. The transport device according to claim 1, wherein said liquid is water.

4. The transport device according to claim 1, wherein the surface of the inner container and/or the outer container is hydrophobic.

5. The transport device according to claim 1, wherein the interstice in which the liquid is disposed has a width in a range of ≥2 mm and ≤15 mm.

6. The transport device according to claim 1, wherein the inner container and/or the outer container comprises a material that is a thermal insulator.

7. The transport device according to claim 1, wherein the outer container further comprises a second section comprising a shell on the inside having the shape of a spherical cap, with an inner diameter and an opening, wherein the opening of the spherical cap of the shell of the second section faces downwards.

8. The transport device according to claim 1, further comprising at least one selected from the group consisting of:
   a) a heating unit,
   b) a cooling unit
   c) a temperature sensor and/or recorder,
   e) an acceleration sensor and/or recorder,
   f) a geolocalization sensor and/or recorder,
   g) an identifiable tag or label, and/or
   h) a mechanical actuator moving the center of gravity with respect to the center of the sphere.

9. The transport device according to claim 1, further comprising a payload, wherein the payload is at least one selected from the group consisting of: one or more multiwell plates or microtiter plates, or a container comprising one or more such plates, microfluidic system or microfluidic chips, and/or cell culturing dishes and systems.

10. The transport device according to claim 1, wherein the outer container and/or the inner container comprise a material selected from the group consisting of: extruded polystyrene foam, expanded polystyrene (EPS), expanded polypropylene (EPP), metal, wood, thermoplasts, and friction-minimizing material.

11. The transport device according to claim 10, wherein the friction-minimizing material is Polytetrafluoroethylene (PTFE).

12. The transport device according to claim 1, wherein the inner container comprises two parts, wherein a first part of the two parts is provided by the upper section and a second part of the two parts is provided by the lower section.

13. The transport device according to claim 1, wherein the liquid reaches maximally up to a height of 25% of a height of the inner container.

14. The transport device according to claim 1, wherein the upper section and the lower section of the inner container are sealed together.

15. The transport device according to claim 1, wherein when the inner container is received within the outer container, the inner container has a geometric center that is outside of the spherical cap of the first section of the outer container.

* * * * *